United States Patent
Samson-Himmelstjerna et al.

(10) Patent No.: US 10,473,745 B2
(45) Date of Patent: Nov. 12, 2019

(54) MAGNETIC RESONANCE SYSTEM FOR GENERATING MAGNETIC RESONANCE DATA OF A FLOWING FLUID

(71) Applicant: FRAUNHOFER-GESELLSCHAFT ZUR FOERDERUNG DER FORSCHUNG E.V., Munich (DE)

(72) Inventors: Federico Von Samson-Himmelstjerna, Munich (DE); Matthias Guenther, Bremen (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 161 days.

(21) Appl. No.: 15/128,532

(22) PCT Filed: Mar. 25, 2015

(86) PCT No.: PCT/EP2015/056419
§ 371 (c)(1),
(2) Date: Sep. 23, 2016

(87) PCT Pub. No.: WO2015/144768
PCT Pub. Date: Oct. 1, 2015

(65) Prior Publication Data
US 2018/0180697 A1    Jun. 28, 2018

(51) Int. Cl.
*G01R 33/56* (2006.01)
*G01R 33/563* (2006.01)
(Continued)

(52) U.S. Cl.
CPC ...... *G01R 33/56366* (2013.01); *A61B 5/0263* (2013.01); *G01R 33/5608* (2013.01); *G01R 33/56308* (2013.01); *A61B 5/055* (2013.01)

(58) Field of Classification Search
CPC combination set(s) only.
See application file for complete search history.

(56) References Cited

U.S. PATENT DOCUMENTS 7,292,720 B2 *  11/2007  Horger ............... A61B 5/055
                                                     382/131
7,369,888 B2 *   5/2008  Alsop ................ A61B 5/0263
                                                     600/419
(Continued)

FOREIGN PATENT DOCUMENTS

WO    WO 2007/035824 A2    3/2007

OTHER PUBLICATIONS

Teeuwisse et al., "Time-Encoded pseudoContinuous Arterial Spin Labeling: Basic Properties and Timing Strategies for Human Applications," Magnetic Resonance in Medicine, 72:1712-1722, (2014).
(Continued)

*Primary Examiner* — Vinh P Nguyen
(74) *Attorney, Agent, or Firm* — Preti Flaherty Beliveau & Pachios LLP (57) ABSTRACT

A magnetic resonance system for generating magnetic resonance data of a flowing fluid is featured. A plurality of magnetic resonance measurements are carried out, wherein in each measurement a) the fluid is either magnetically labeled or not labeled at different first points in time in a first region, so as to generate a flowing sequence of labeled and/or unlabeled fluid boli, and b) first magnetic resonance data are measured at a second point in time in a second region. Second magnetic resonance data are determined, each of which are indicative of a combination fluid bolus—combined from a plurality of fluid boli generated at different first points in time and flowing to the second region—and a time interval between one of the first points in time and the second point in time, based on a combination of the first
(Continued)

magnetic resonance data measured in the different magnetic resonance measurements.

22 Claims, 4 Drawing Sheets

(51) Int. Cl.
  *A61B 5/026* (2006.01)
  *A61B 5/055* (2006.01)

(56) References Cited

U.S. PATENT DOCUMENTS

| | | |
|---|---|---|
| 8,260,396 B2 * | 9/2012 | Guenther ............ A61B 5/0263 324/307 |
| 9,675,249 B2 * | 6/2017 | Miyazaki ........... G01R 33/5614 |
| 2012/0293171 A1 | 11/2012 | Dannels et al. |

OTHER PUBLICATIONS

Wells et al., "In Vivo Hadamard Encoded Continuous Arterial Spin Labeling (H-CASL)," Magnetic Resonance in Medicine, 63:1111-1118 (2010).

Von Samson-Himmelstjerna et al., "Time efficient and robust perfusion measurement using Walsh-reordered time encoded pCASL," Proc. Intl. Soc. Mag. Reson. Med., 22:0719 (2014).

* cited by examiner

MAGNETIC RESONANCE SYSTEM FOR GENERATING MAGNETIC RESONANCE DATA OF A FLOWING FLUID

The invention relates to a magnetic resonance system (MR system), to an MR method and to a computer program for generating MR data of a flowing fluid. The invention furthermore relates to an evaluation system, an evaluation method and a computer program for evaluating MR data of a flowing fluid. The fluid is preferably blood.

U.S. Pat. No. 8,260,396 B2 (Guenther 2012) discloses an MR system, which magnetically labels in vivo blood within predeterminable spatial sections of the vessels, e.g. in the region of the carotid artery. This takes place there by means of an arterial MR spin labeling process, also called arterial spin labeling (ASL). These blood sections are called boli (singular bolus) and represent spatially defined regions of either labeled or unlabeled blood within a vessel. As is well-known, the latter serve as control or also comparison sections and are often also referred to as such. In the MR system described in (Guenther 2012), the blood sections are magnetically labeled or not labeled at consecutive first points in time, thus creating a flowing sequence of label and control boli. Different boli sequences are generated by means of different combinations of label and control boli. The different sequences of label/control boli represent different codings of the blood in a technically functional manner. A Hadamard matrix, the elements of which determine whether a label or a control bolus is generated and wherein each row of the matrix determines a sequence of label and/or control boli, is preferably used here for the coding. Each row of the matrix thus forms the basis for an MR measuring of first MR data. After a wait time (often also called inflow time (TI), first MR images, which are also called intermediate images, are determined in a second region for each of these blood boli sequences. This second region is the region, to which the blood boli sequence flows, for example the brain in the case of Guenther. These first MR images are then combined in the known manner in the decoding step, they are in particular added to one another or are subtracted from one another. For the decoding, the Hadamard matrix, which is used for the coding, is preferably inverted first and is then used in the actual decoding step to determine the mathematical operations, which are necessary for the combining. For this purpose, in particular the second MR data are added to one another or are subtracted from one another, depending on the entry of a row of the matrix. Second MR images, each of which are indicative of an individual blood bolus generated at a certain first point in time and flowing to the second region, are decoded in this manner. They each correspond to a first MR image, which would have been determined, if only an individual selected labeled blood bolus would have been generated at the first point in time. The different second MR images thereby still correspond to different TIs. The MR system described by Guenther 2012 is highly efficient, because clinically relevant MR data relating to organ perfusion and/or circulation can be gained with said system within a comparatively short period of time and without deterioration of the signal-noise ratio. In the case of an exemplary implementation of (Guenther 2012), N−1 reconstructed images can be generated from N measured MR images and all N measured MR images are required to generate each of these N−1 reconstructed MR images. An MR signal can be determined at different wait times TI by means of the N−1 reconstructed MR images and the signal course can thus be determined voxel by voxel/pixel by pixel over time. Different parameters, which are relevant for the clinical diagnosis, can then be determined voxel by voxel/pixel by pixel from these signal-time curves.

It is an object of the invention at hand to provide an MR system, a MR method and a corresponding computer program, which make it possible to improve the generation of MR data of a flowing fluid.

The object is solved by means of an MR system for generating MR data of a flowing fluid, wherein the MR system has:
  a data collection unit for collecting first MR data, wherein the data collecting unit is adapted to carry out a plurality of MR measurements, wherein first MR data are measured in every MR measurement, in that
    a) the fluid is either magnetically labeled or not labeled at different first points in time in a first region so as to generate a flowing sequence of labeled and/or unlabeled fluid boli, and
    b) the first MR data, which are indicative of the generated sequence of labeled and/or unlabeled fluid boli, are measured at a second point in time in a second region, to which the fluid flows, starting at the first region,
  an evaluation unit for evaluating the first MR data measured in the different MR measurements, wherein the evaluation unit is adapted to determine second MR data, each of which are indicative of a combination fluid bolus—combined from a plurality of fluid boli generated at different first points in time and flowing to the second region—and a time interval between one of the first points in time and the second point in time, based on a joining of the first MR data measured in the different MR measurements.

The labeling/non-labeling according to above-mentioned feature a) can also be seen as coding of the fluid—as has already been done in Guenther 2012. As is well known (see Guenther 2012), the joining mentioned above, which could also be identified as a combination, consists in particular of mathematical operations, such as addition and subtraction of the first MR data.

By using the combination fluid bolus/boli, the possibility, which will be explained in more detail below, is created, to obtain information relating to the flow behavior of the fluid before all of the first MR data have been measured. It is thus not necessary, for example, to wait for a complete measuring process and to determine the second MR only then, as it is described, for instance, in the above-mentioned publication Guenther 2012. The MR system can improve the generation of MR data of a flowing fluid in particular in this sense.

As a result, a comparatively longer bolus, which has been called combination fluid bolus above, is effectively created by the combination of the combination fluid bolus of two or more consecutively labeled/unlabeled individual fluid boli. A combination fluid bolus can thus also be understood as a sequence of two or more individual fluid boli.

Even though the richness of detail of the second MR data decreases with fewer fluid boli, which become longer, that is, ultimately with larger chronological scanning steps, it is possible to generate the second MR data from fewer first MR data and to thus also gain relevant second MR data at an earlier point in time, for instance clinically relevant statements relating to the organ perfusion. This information can advantageously also be considered in response to the further control of the MR measurement.

Applicant hereby expressly reserves the right to claim independent patent protection for the following technical information: To initially start with longer fluid boli when determining the second MR data from the first MR data, and to then transition to shorter fluid boli.

The flowing fluid is preferably blood. However, the flowing fluid can also be a different liquid or gaseous substance; for example also a different bodily fluid. The first MR data are preferably two-dimensional or three-dimensional MR images consisting of pixels or voxels.

It is preferred for the evaluation unit to further be adapted to determine second MR data, each of which are indicative of individual fluid boli generated at a certain first point in time and flowing to the second region, based on a joining of the first MR data measured in the different MR measurements. That is, in one embodiment, the evaluation unit cannot only be adapted to combine the first MR data measured in the different MR measurements so as to determine second MR data, each of which are indicative of a combination fluid bolus—combined from a plurality of fluid boli generated at a different first points in time and flowing to the second region, but the evaluation unit can also be adapted to join the first MR data measured in the different MR measurements, so as to determine second MR data, each of which are indicative of an individual fluid bolus generated at a certain first point in time and flowing to the second region. The evaluation unit can thus be adapted to determine second MR data, each of which are indicative of a comparatively longer composite combination fluid bolus, and so as to furthermore determine second MR data, each of which are indicative of a comparatively shorter individual fluid bolus.

It is furthermore preferred for the evaluation unit to be adapted in such a manner that fewer first MR data are used to determine those second MR data, each of which are indicative of a combination fluid bolus and of a time interval between one of the first points in time and one of the second points in time, than are used to determine those second MR data, each of which are indicative of an individual fluid bolus. This means that second MR data, each of which are indicative of a combination fluid bolus and a time interval between one of the first points in time and the second point in time, can nonetheless be determined when, for example, some first MR data should be inaccurate, for example because a patient has moved, so that second MR data, each of which are indicative of an individual fluid bolus, can thus not be determined. In addition, second MR data, each of which are indicative of a combination fluid bolus and a time interval between one of the first points in time and the second point in time, could on principle already be determined before all of the first MR data, which are required to determine the second MR data, each of which are indicative of an individual fluid bolus, have been measured. It is possible, for example, that those second MR data, each of which are indicative of a combination fluid bolus and a time interval between one of the first points in time and the second point in time, are already determined in real time during the measurement.

The MR system preferably has a matrix provision unit for providing a two-valued determination matrix, that is, a matrix, the elements of which have one of two possible values. One row of the determination matrix thereby represents a sequence of labeled and/or unlabeled fluid boli, wherein different rows of the determination matrix form the basis for different MR measurements of the first MR data. The determination matrix can also be perceived as matrix, which determines the coding of the fluid boli. The evaluation unit is furthermore adapted a) to form a vector, wherein a vector element is formed by means of an MR value of the first MR data and different vector elements correspond to different MR measurements of the first MR data, b) to invert the determination matrix, and c) to determine the second MR data, in that the inverted determination matrix is applied to the vector, in particular multiplied by it. The entries of a two-valued determination matrix only have two values, for example +1 and −1, which represent labeled and unlabeled fluid boli. The determination matrix thus comprises a plurality of matrix elements, wherein each of these matrix elements can have one of two possible values. The expression "two-valued" thus refers to the number of possible values of a matrix element. However, it does not refer to the number of the matrix elements, for example.

A first MR value, that is, an MR value of the first MR data, which forms a vector element, is preferably an image value, in particular a voxel value or a pixel value, of a first MR image. This means that the determination of the second MR data can take place pixel by pixel or voxel by voxel, respectively, wherein a vector is formed for each pixel or for each voxel, respectively, of the different first MR images, which represent the first MR data in this example. A vector, which has the corresponding image values at the locations (1, 1) of the first MR images recorded at the different first points in time, is formed for the pixel at the location (1, 1), for example.

In one embodiment, first MR images, for example, are thus joined, in particular added and/or subtracted, in the decoding step (such a step is already known on principle from Guenther 2012) as first MR data, so as to generate second MR images as second MR data. In one embodiment, the generation of a second MR image by joining a plurality of first MR images can take place in that the first MR images are added and/or subtracted according to the entries of one row of the inverted determination matrix to form a second MR image. The inverted determination matrix can also be perceived as decoder matrix here. Mathematically, this can be realized as follows, for example: a vector is formed, in the case of which each vector entry is assigned exactly to a first MR image and corresponds to the voxel value at exactly one predetermined voxel location of the respective first MR image. The inverted determination matrix is then multiplied by this vector. The result is a second vector, in the case of which each vector entry is in turn assigned to exactly a second MR image and corresponds to the voxel value at the same, predetermined voxel location of the respective MR image. In the described embodiment, this method is carried out for each voxel of the first and second MR images. So as to determine a voxel value for the voxel location (1, 1, 1) of a second MR image, for example, a first row of the inverted determination matrix can be multiplied by a vector, which has the voxel values included in the different first MR images at the voxel location (1, 1, 1). So as to determine the voxel value, which is arranged at the location (1, 1, 2) for this second MR image, the same first row of the inverted determination matrix can be multiplied by a vector, which has the voxel values of the first MR images at the voxel location (1, 1, 2). This is carried out for all voxels, so that the voxel values of all voxel positions for this second MR image are determined in this way. Different rows of the inverted determination matrix then each correspond to exactly one second MR image.

It is preferred that, for each sequence of labeled and/or unlabeled fluid boli, the data collection unit is furthermore adapted to generate a sequence, which is complementary thereto, wherein a first sequence is complementary to a second sequence, if an unlabeled fluid bolus is arranged at every location of the first sequence, which corresponds to a location of the second sequence, and vice versa. In one embodiment, a first MR image is generated for each flowing sequence of labeled and/or unlabeled fluid boli. Due to the fact that a complementary sequence is present for each sequence of labeled and/or unlabeled fluid boli, a further first MR image, which was generated on the basis of a flowing sequence of labeled and/or unlabeled fluid boli, which is complementary to the flowing sequence of labeled and/or unlabeled fluid boli, on which the previous first MR image is based, is preferably generated for each first MR image. In a preferred embodiment, a further first MR image, which was generated on the basis of a flowing sequence, which is complementary to the first sequence, thus exists for each first MR image, which was generated on the basis of a first flowing sequence.

In contrast to the above-mentioned publication Guenther 2012, the provision of sequences, which are complementary to each other, of labeled/unlabeled fluid boli, has the following advantage, for example: only N−1 second MR data can be determined therein from N first MR data, for example second MR data, which are indicative of the first fluid bolus, cannot be generated. However, when using the information from the two complementary fluid boli sequences, second MR individual data, which are indicative of all N fluid boli, can be generated. Second MR combination data, which are indicative of the combination fluid boli, which include the first fluid bolus, can then also be generated from the first MR data.

For providing complementary fluid boli sequences, applicant hereby expressly also reserves the right to separate, that is, independent patent protection; likewise for the application and use thereof, for example when determining the second MR data.

It is furthermore preferred for the data collection unit to be adapted to carry out MR measurements of the first MR data, which have complementary sequences, one immediately after the other. This means that in one embodiment, a second such MR measurement with a second sequence, which is complementary to the first sequence, is carried out after a first MR measurement with a first fluid boli sequence, after which third and fourth MR measurements of first MR data with third and fourth sequences are carried out, wherein the fourth sequence is complementary to the third sequence, and so forth. The data collection unit can accordingly be programmed such, for example, that it initially generates a first MR image, which is based on a first flowing sequence of labeled and/or unlabeled fluid boli, after which a further first MR image is generated, which is based on a second sequence of labeled and/or unlabeled fluid boli, which is complementary to the first sequence. A further first MR image, which is based on a third sequence of labeled and/or unlabeled fluid boli, can then be generated by means of the correspondingly programmed data collection unit, after which a further first MR image can be generated, which is based on a fourth sequence of labeled and/or unlabeled fluid boli, which is complementary to the third sequence of labeled and/or unlabeled fluid boli, and so forth.

In one embodiment, the MR system comprises a matrix provision unit for providing a two-valued first determination matrix, the rows of which represent a first group of sequences of labeled and/or unlabeled fluid boli and wherein different rows of the first determination matrix form the basis for different MR measurements of the first MR data. In addition, the matrix provision unit is adapted to provide a second two-valued determination matrix, the rows of which represent a second group of sequences of labeled and/or unlabeled fluid boli, which are complementary to the sequences of the first group, and wherein different rows of the second determination matrix correspond to the different MR measurements of the first MR data. The evaluation unit is furthermore adapted a) to form a first vector, wherein a vector element of the first vector is in each case formed by an MR value of the first MR data, and different vector elements of the first vector correspond to different MR measurements, which, in turn, correspond to different sequences of the first group, b) form a second vector, wherein a vector element of the second vector is formed by an MR value of the first MR data and different vector elements of the second vector correspond to different MR measurements, which, in turn, correspond to different sequences of the second group, c) to invert the first determination matrix and the second determination matrix, and d) to determine the second MR data, in that the inverted first determination matrix is applied to the first vector and the inverted second determination matrix is applied to the second vector, in particular by multiplication. The first determination matrix is preferably formed by means of a Hadamard matrix and the second determination matrix is preferably formed by a Hadamard matrix, which is multiplied by −1 and which thus corresponds to the complementary sequences of labeled and/or unlabeled fluid boli and which can also be identified as complementary Hadamard matrix.

In one embodiment, there is thus a first group of sequences of labeled and/or unlabeled fluid boli, wherein a first MR image can in each case be generated for each sequence of this first group. Due to the fact that the lines of the first determination matrix represent the sequences of labeled and/or unlabeled fluid boli of the group and due to the fact that a respective sequence of labeled and/or unlabeled fluid boli characterizes an MR measurement, in response to which a respective first MR image was generated, a single row of the first determination matrix corresponds to an individual MR measurement, which resulted in an individual first MR image, and different lines of the first determination matrix correspond to different MR measurements, which resulted in different first MR images.

In one embodiment, the first determination matrix is inverted and the inverted first determination matrix is multiplied by a first vector, which has the different voxel values of the different first MR images at the same voxel location (1, 1, 1) so as to calculate voxel values at the same voxel location (1, 1, 1) for second MR images. A first vector is also in each case generated for the other voxel locations and is multiplied by the inverted first determination matrix, so as to generate voxel values at the corresponding voxel locations for the second MR images. A first group of second MR images is generated in this manner for the first group of sequences of labeled and/or unlabeled fluid boli. A second determination matrix for a second group of sequences of labeled and/or unlabeled fluid boli can be generated and inverted in the same manner, wherein the inverted second determination matrix can be multiplied by corresponding second vectors, so as to also generate second MR data for the second group of sequences of labeled and/or unlabeled fluid boli.

The data collection unit is preferably adapted to carry out MR measurements sorted chronologically one after the other according to the number of changes between labeled and/or unlabeled fluid boli in the corresponding sequence. The MR measurements are preferably sorted chronologically according to a Walsh sorting. This means that the above-described determination matrix preferably has lines, which are arranged according to the Walsh sorting. In one embodiment, a data collection unit, that is, in particular a corresponding MR system, can thus be set in such a way that a first MR image is generated first on the basis of a sequence of labeled and/or unlabeled fluid boli, which has the smallest number of changes between labeled and/or unlabeled fluid boli. Next, a further first MR image could be generated on the basis of a sequence, which has the second lowest amount of changes between labeled and/or unlabeled fluid boli, and so forth. If several sequences have the same number of changes between labeled and/or unlabeled fluid boli, the corresponding first MR images are generated successively, before a further first MR image is generated, which is based on a sequence, which has a larger number of changes between labeled and/or unlabeled fluid boli.

In a preferred embodiment, the evaluation unit is adapted to determine addition and/or subtraction data, in that first MR data, which are measured in different MR measurements, are added to and/or subtracted from one another, so as to determine the second MR data based on the addition and/or subtraction data. This means for example, that corresponding pixel values or voxel values of first MR images of different MR measurements are added and/or subtracted so as to determine the second MR data, each of which are indicative of a combination fluid bolus—combined from a plurality of fluid boli generated at different first points in time and flowing to the second region—and a time interval between one of the first points in time and the second point in time.

The above-mentioned object of improving the generation of MR data of a flowing fluid is furthermore solved by means of an evaluation system for evaluating MR data of a flowing fluid, wherein the evaluation system has:
  a data provision unit for providing first MR data, wherein the data provision unit is adapted to provide first MR data of a plurality of MR measurements, wherein first MR data were measured in each MR measurement, in that
    a) the fluid was either magnetically labeled or not labeled at different first points in time in a first region, so as to generate a flowing sequence of labeled and/or unlabeled fluid boli, and
    b) the first MR data, which are indicative of the generated sequence of labeled and/or unlabeled fluid boli, were measured at a second point in time in a second region, to which the fluid flows, starting at the first region,
  an evaluation unit for evaluating the first MR data measured in the different MR measurements, wherein the evaluation unit is adapted to determine second MR data, each of which are indicative of a combination fluid bolus—combined from a plurality of fluid boli generated at different first points in time and flowing to the second region—and a time interval between one of the first points in time and the second point in time, based on a joining of the first MR data measured in the different MR measurements.

The above-mentioned object is furthermore solved by means of an MR method for generating MR data of a flowing fluid, wherein the MR method has:
  collecting first MR data, wherein a plurality of MR measurements are carried out and wherein first MR data are measured in each MR measurement, in that
    a) the fluid is either magnetically labeled or not labeled at different first points in time in a first region, so as to generate a flowing sequence of labeled and/or unlabeled fluid boli, and
    b) the first MR data, which are indicative of the generated sequence of labeled and/or unlabeled fluid boli, are measured at a second point in time at a second location, to which the fluid flows, starting at the first region,
  evaluating the first MR data measured in the different MR measurements, wherein the evaluation unit is adapted to determine second MR data, each of which are indicative of a combination fluid bolus—combined from a plurality of fluid boli generated at different first points in time and flowing to the second region—and a time interval between one of the first points in time and the second point in time, based on a joining of the first MR data measured in the different MR measurements.

The above-mentioned object is furthermore solved by means of an evaluation method for evaluating MR data of a flowing fluid, wherein the evaluation method has:
  providing first MR data, wherein first MR data of a plurality of MR measurements are provided, wherein first MR data were measured in each MR measurement, in that
    a) the fluid was either magnetically labeled or not labeled at different first points in time in a first region, so as to generate a flowing sequence of labeled and/or unlabeled fluid boli, and
    b) the first MR data, which are indicative of the generated sequence of labeled and/or unlabeled fluid boli, were measured at a second point in time in a second region, to which the fluid flows, starting at the first region,
  evaluating the first MR data measured in the different MR measurements, wherein second MR data are determined, each of which are indicative of a combination fluid bolus—combined from a plurality of fluid boli generated at different first points in time and flowing to the second region—and a time interval between one of the first points in time and the second point in time, based on a joining of the first MR data measured in the different MR measurements.

The above-mentioned object is also solved by means of a computer program for generating MR data of a flowing fluid, wherein the computer program has program code means, which have the result that the MR system according to claim 1 carries out the MR method according to claim 10, when the computer program is executed on a computer, which controls the MR system.

The above-mentioned object is furthermore solved by means of a computer program for evaluating MR data of a flowing fluid, wherein the computer program has program code means, which have the result that the evaluating system according to claim 9 carries out the evaluating method according to claim 11, when the computer program is executed on a computer, which controls the evaluation system.

It should be understood that the MR system according to claim 1, the evaluation system according to claim 9, the MR method according to claim 10, the evaluation method according to claim 11 and the computer programs according to claims 12 and 13 have similar and/or identical preferred embodiments, as they are defined in particular in the dependent claims.

It should furthermore be understood that a preferred embodiment of the invention at hand can be formed by every combination of the dependent claims and/or of the embodiments mentioned in the application at hand with the respective independent claims.

Embodiments of the invention will be described by referring to the Figures below, wherein.

Figure 1:
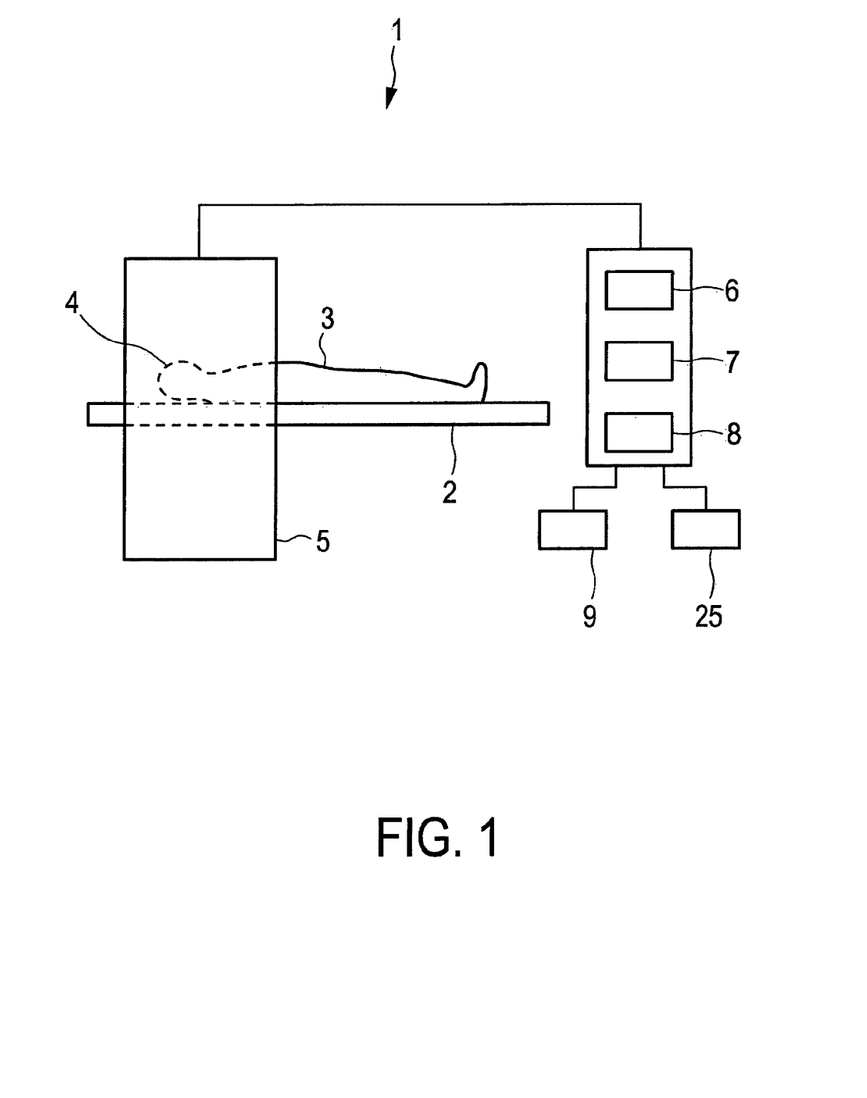
FIG. 1 shows an embodiment of an MR system in a schematic and exemplary manner.

FIG. 1 shows an embodiment of an MR system in a schematic and exemplary manner. The MR system 1 comprises a data collection unit 5 for collecting first MR data of a patient 3, who is arranged on a patient table 2. In this embodiment, the data collection unit 5 is embodied to carry out a plurality of MR measurements in the head region 4 of the patient 3. In each MR measurement, first MR data are measured in that a) the blood, which flows in one or a plurality of blood vessels, in particular arteries, is either magnetically labeled or not labeled in a first vessel section of the patient 3 at different first points in time, so as to generate a flowing sequence of labeled and/or unlabeled fluid boli, here labeled and/or unlabeled blood boli (FIG. 2; L,C), and b) the first MR data, which are indicative of the generated sequence of labeled and/or unlabeled blood boli, are measured at a second point in time in a second region, to which the blood flows, starting at the first location, that is, the above-mentioned vessel section. The MR system 1 furthermore has an evaluation unit 7 for evaluating the first MR data measured in the different MR measurements, wherein the evaluation unit 7 is adapted to determine second MR data, each of which are indicative of a combination fluid bolus—combined from a plurality of fluid boli generated at different first points in time and flowing to the second region—and a time interval between one of the first points in time and the second point in time. The determination of the second MR data is based on a joining of the first MR data measured in the different MR measurements. This joining comprises in particular an adding and subtracting of first MR data, wherein in particular the elements of a decoding matrix determine, whether a subtraction of addition takes place. This can also be described, for example analogous to Guenther 2012, by a multiplication of the decoding matrix by a vector, the individual entries of which are formed by an image value, e.g. the value of a voxel, in each case of one of the first MR data. The evaluation unit 7 is furthermore adapted to also determine such second MR data, each of which are indicative of an individual blood bolus generated at a certain first point in time and flowing to the second region, in turn based on a joining of the first MR data measured in the different MR measurements. In this embodiment, the first and second MR data are MR images.

The MR system 1 furthermore has a matrix provision unit 6 for providing a two-valued determination matrix, wherein each row of the determination matrix is formed by a sequence of labeling and/or non-labeling regions. These labeling/non-labeling regions determine, whether the blood is labeled or not labeled and they correspond to the labeled/unlabeled blood boli in this respect. The determination matrix thus contains the rule for the coding of the individual blood boli. The different MR measurements of the first MR data correspond to different lines of the determination matrix, more exactly to different sequences of blood boli, which were coded in accordance with the determination matrix. The evaluation unit 7 is also adapted to form a vector, wherein a vector element is formed by a first MR value, which corresponds to an image value in this embodiment, and different vector elements correspond to different MR measurements. The evaluation unit 7 is furthermore adapted to invert the determination matrix—thus to turn it into a decoding matrix—and to determine the second MR data, in that the inverted determination matrix is applied to the vector.

16 MR measurements are carried out in this exemplary embodiment, wherein a sequence of eight labeled and/or unlabeled blood boli is generated in each MR measurement. The coding of the sequences of blood boli in the different MR measurements can be represented, for example, by the following matrix M in this case:

$$M = \begin{pmatrix} +1 & +1 & +1 & +1 & +1 & +1 & +1 & +1 \\ -1 & -1 & -1 & -1 & -1 & -1 & -1 & -1 \\ +1 & +1 & +1 & +1 & -1 & -1 & -1 & -1 \\ -1 & -1 & -1 & -1 & +1 & +1 & +1 & +1 \\ +1 & +1 & -1 & -1 & -1 & -1 & +1 & +1 \\ -1 & -1 & +1 & +1 & +1 & +1 & -1 & -1 \\ +1 & +1 & -1 & -1 & +1 & +1 & -1 & -1 \\ -1 & -1 & +1 & +1 & -1 & -1 & +1 & +1 \\ +1 & -1 & -1 & +1 & +1 & -1 & -1 & +1 \\ -1 & +1 & +1 & -1 & -1 & +1 & +1 & -1 \\ +1 & -1 & -1 & +1 & -1 & +1 & +1 & -1 \\ -1 & +1 & +1 & -1 & +1 & -1 & -1 & +1 \\ +1 & -1 & +1 & -1 & -1 & +1 & -1 & +1 \\ -1 & +1 & -1 & +1 & +1 & -1 & +1 & -1 \\ +1 & -1 & +1 & -1 & +1 & -1 & +1 & -1 \\ -1 & +1 & -1 & +1 & -1 & +1 & -1 & +1 \end{pmatrix} \quad \text{(equation 1)}$$

"−1" hereby identifies a non-labeling region and "+1" identifies a labeling region, thus determines, whether the respective blood bolus is not labeled or labeled. For each sequence of labeled and/or unlabeled blood boli, that is, for each row, the matrix M has a complementary sequence, wherein complementary sequences are arranged directly behind one another. The individual sequences are also sorted according to the number of changes between labeled and unlabeled blood boli. This means that the lines of the matrix M are preferably Walsh-sorted. The Walsh-sorting is described, for example, in Wolfram, S., 2002. *A new kind of science* 1st ed., Wolfram Media, Inc. and Wang, R., 2013. Sequency Ordered Walsh-Hadamard Matrix, http://fourier.eng.hmc.edu/e161/lectures/wht/node3.html (Wolfram 2002).

Figure 2:
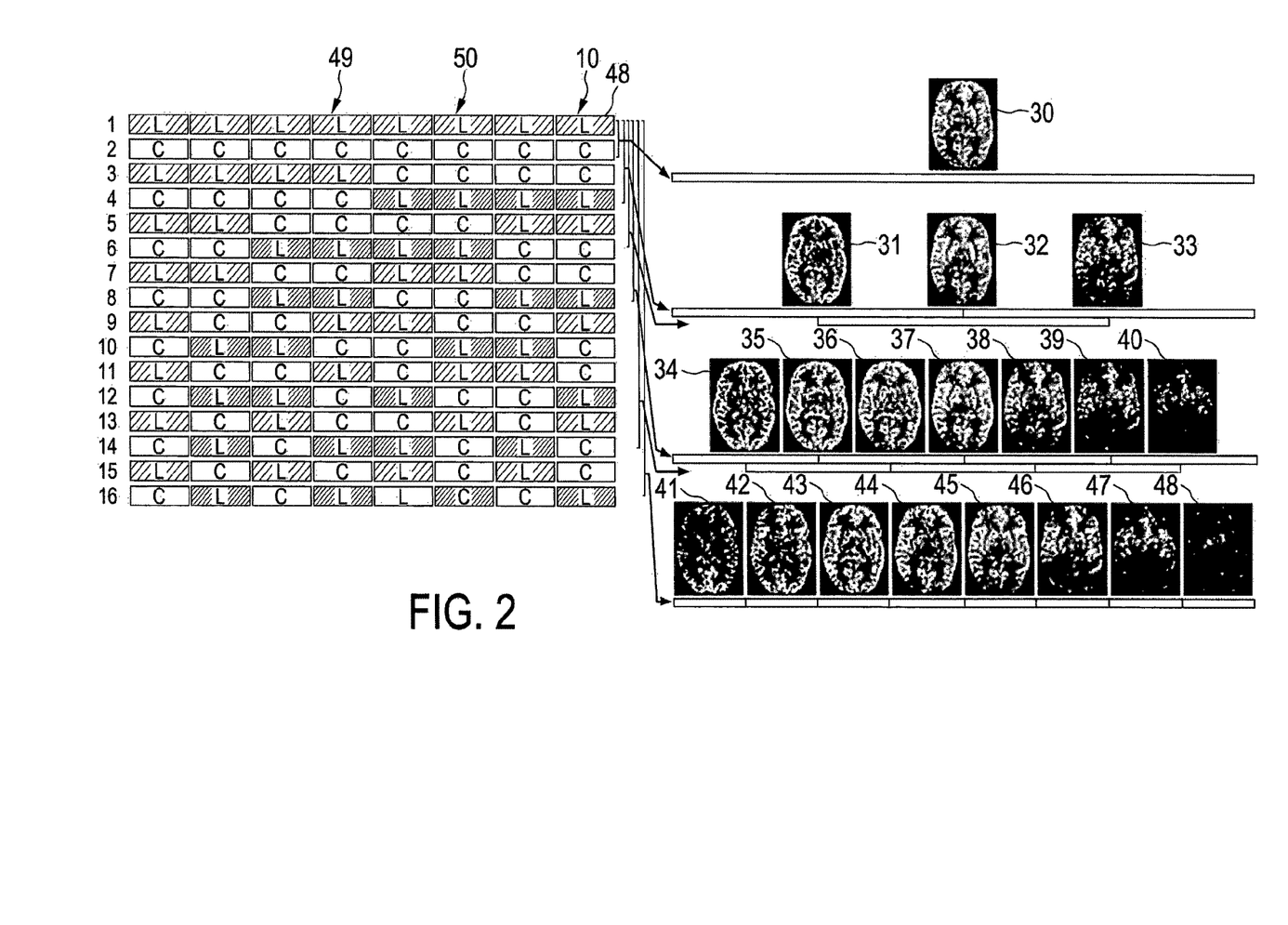
FIG. 2 shows different sequences of labeled and unlabeled fluid boli and second MR data in a schematic and exemplary manner.

The matrix M can be formed by means of a combination of a first determination matrix, which, in this example, is a Hadamard matrix, with a second determination matrix, which, in this, example, is a complementary Hadamard matrix, that is, a matrix, which corresponds to the complementary sequences of labeled and/or unlabeled fluid boli, wherein the lines of the Hadamard matrix and of the complementary Hadamard matrix are used alternately for generating the matrix M. The individual sequences of labeled and unlabeled blood boli, which correspond to the individual lines of the matrix M, are illustrated schematically and in an exemplary manner in FIG. 2. FIG. 2 shows 16 sequences 10 of labeled boli L and unlabeled boli C, which can also be perceived as control boli. In FIG. 2, the sequences identified with odd numbers (lines 1, 3, 5, . . . , 15), which can also be identified as sequences of a first group, correspond to lines of the Hadamard matrix, and the sequences identified with even numbers (lines 2, 4, 6, . . . , 16), which can also be identified as sequences of a second group, correspond to lines of the complementary Hadamard matrix.

The second MR data obtained from the first MR data, each of which are indicative of a blood bolus generated at a certain first point in time and flowing to the second region, are preferably determined voxel by voxel. This means that the first MR data are preferably first MR images comprising different voxels, wherein a first vector and a second vector are furthermore formed. A vector element of the first vector is formed by a voxel value of a first MR image, wherein different vector elements of the first vector correspond to different MR measurements, which, in turn, correspond to different sequences of the first group (lines 1, 3, 5, ..., 15). A vector element of the second vector is formed by a voxel value of a second MR image, wherein different vector elements of the second vector correspond to different MR measurements, which, in turn, correspond to different sequences of the second group (lines 2, 4, 6, ..., 16). For example, a first vector for the voxel (1, 1, 1) has the voxel values for this voxel in the different first MR images, which were generated in the different MR measurements, which correspond to the different sequences of blood boli of the first group (lines 1, 3, 5, ..., 15). For each voxel, second MR data, i.e. voxel values for the corresponding voxel, each of which are indicative of a blood bolus generated at a certain first point in time and flowing to the second region, are thus preferably generated, in that the inverse first determination matrix is multiplied by the first vector and the inverse second determination matrix is multiplied by the second vector for each voxel. The two resulting vectors can be averaged, for example, wherein the resulting averaged vector represents the second MR data, for example for the voxel (1, 1, 1).

The evaluation unit 7 is furthermore adapted in such a way that, for determining the second MR data, each of which are indicative of a combination blood bolus—combined from a plurality of blood boli generated at different first points in time and flowing to the second region—and a time interval between one of the first points in time and the second point in time, fewer first MR data are combined than for the determination of the second MR data, each of which are indicative of a individual blood bolus generated at a certain first point in time and flowing to the second region. This will be explained in an exemplary manner below with reference to FIG. 2.

In this exemplary embodiment, the evaluation unit 7 subtracts the first MR image of the first MR measurement, which is based on the first row of the first group (row 1) of the blood boli sequences 10, from the first MR image of the second MR measurement, which is based on the first row of the second group (row 2) of the blood boli sequences 10, so as to generate the second MR image 30, that is, corresponding second MR data. The second MR image 30 is indicative of the combination blood bolus, which is formed from all eight individual blood boli, thus has eight times the length of an individual blood bolus, and of the time interval TI between the second point in time, at which the first MR images were recorded, and the second point in time, at which the blood bolus 48 was labeled. From the perspective of a combination blood bolus, the individual blood boli could also be identified as subboli. The second MR images 31, 32, 33 each correspond to a combination blood bolus, which is formed from four individual blood boli, thus has four times the length of an individual blood bolus. The second MR image 31 was generated in that the first MR image of the fourth MR measurement ($4^{th}$ row) was subtracted from the first MR image of the first MR measurement ($1^{st}$ row). The second MR image 32 was generated in that the first MR image of the fifth MR measurement ($5^{th}$ row) was subtracted from the first MR image of the first MR measurement ($1^{st}$ row), and the second MR image 33 has been generated in that the first MR image of the third MR measurement ($3^{rd}$ row) has been subtracted from the first MR image of the first MR measurement ($1^{st}$ row). The second MR image 31 corresponds to a time interval TI between the second point in time and the point in time, at which the blood bolus 49 was labeled. The second MR image 32 corresponds to a time interval TI between the second point in time and the point in time, at which the blood bolus 50 was labeled, and the second MR image 33 corresponds to a time interval TI between the second point in time and the point in time, at which the blood bolus 48 was labeled. The length of the individual or combination blood boli, which were used to generate the second MR images 30-48 depicted in FIG. 2, is illustrated once again below the corresponding images in the form of horizontal bars. The subtracting and adding of MR images measured successively is a basic principle in the case of time-coded ASL (see Guenther 2012). The Walsh sorting of the determination matrix carried out here ensures automatically that, with an increasing number of MR measurements, combination blood boli, which become shorter and shorter, form the basis for the decoded second MR images.

A method for determining the decoding rules of the second MR images from the first MR images for matrixes of any size and according to which the images 30-48, for example, were determined as well, can look as follows, for example. Initially, it is written symbolically, that is, written in symbols, for each second MR image, each of which is indicative of a single fluid bolus, that is, individual fluid bolus generated at a certain first point in time and flowing to the second region, how these second MR images $b_1, \ldots, b_N$ made up of first MR images $v_1, \ldots, v_N$, or how the $v_i$ are joined to the $b_i$, respectively.

For example by means of the first group (lines 1, 3, 5, ..., 15) of matrix M (see equation 1) (the second group (lines 2, 4, 6, ..., 16 of the matrix M) can be treated analogously as well):

$$b_2 = \tfrac{1}{8}(v_1 + v_2 + v_3 + v_4 - v_5 - v_6 - v_7 - v_8)$$

It is important to note thereby that this step can already take place symbolically prior to the generation of first MR data and that second MR images are thereby also not generated. The symbolic illustration of the individual fluid boli only serves the purpose of deriving arithmetic calculation rules for the second MR images, each of which are indicative of a combination fluid bolus generated at a certain first point in time and flowing to the second region.

In a second step, all of the desired second MR data $K_i$ are determined symbolically from the $b_i$ by adding and/or subtracting. The approach is thereby such that the fluid boli, for which the $b_i$ are indicative, yield the combination fluid boli, of which the $K_i$ are indicative. After deleting all of the summands, which go towards zero, the arithmetic calculation rule then results for the desired combination fluid bolus from this symbolic way of writing.

For example by means of the first group (lines 1, 3, 5, ..., 15) of matrix M (see equation 1) (the second group (lines 2, 4, 6, ..., 16 of M) can be treated analogously as well):

$$b_2 + b_3 = \tfrac{1}{8}((v_1 + v_2 + v_3 + v_4 - v_5 - v_6 - v_7 - v_8) + (v_1 + v_2 - v_3 - v_4 - v_5 - v_6 + v_7 + v_8))$$

$$= \tfrac{1}{4}(v_1 + v_2 - v_5 - v_6)$$

or also $$b_5 + b_6 + b_7 + b_8 = \tfrac{1}{2}(v_1 - v_2)$$

If, for example, second MR images, which are indicative of the first fluid bolus or combination fluid boli, which include the first fluid bolus, are to be determined as well, first MR images from the first and the second group are combined. In this example, the first fluid bolus refers to that fluid bolus, which has the largest time interval TI between the generation thereof and the second point in time, and the last fluid bolus refers to that fluid bolus, which has the smallest time interval between the generation thereof and the second point in time. To determine the second MR images, which are indicative of the first fluid bolus, the summands with negative sign are simply replaced by entries of the second vector, thus image values of the first MR images $v_i^k$ (second group) belonging to the complementary matrix, with the same indices in the calculation rule for the second MR images, which are indicative of the last fluid bolus. The calculation rules for determining second MR data, which are indicative of combination fluid boli, which include the first fluid bolus, can be adapted analogously.

For example by means of the first (lines 1, 3, 5, . . . , 15) and second (lines 2, 4, 6, . . . , 16) group of matrix M (see equation 1):

$$b_1+b_2+b_3+b_4=\frac{1}{2}(v_1-v_2^k)$$

In this example, the determination of second MR data, which are indicative of the first fluid bolus or combination fluid boli, which include the first fluid bolus, has thus only become possible by combining the information of the determination matrix and the determination matrix complementary thereto.

The second MR images, that is, the second MR data, which correspond to combination fluid boli, or more exactly, which are indicative of them, are generated with fewer first MR data than the second MR data, each of which correspond to individual fluid boli. In particular, second MR data are determined in the latter case for the respective eight individual fluid boli, that is, for the corresponding eight first points in time, in that at least eight first MR images, in particular all 16 first MR images, which correspond to the 16 sequences 10 are combined by using the above-mentioned first and second determination matrixes, in the case of the above-mentioned combined determination matrix (M, see equation 1). In contrast, for example, only two first MR images, for example the first MR images based on lines 1 and 2 of the determination matrix M, are required for the determination of the second MR data, which correspond to the combination fluid boli. The second MR data, which correspond to combination fluid boli, can thus be generated, even if not all 16 first MR images have been recorded. This means that the second MR images, which correspond to the combination fluid boli, can already be generated before all 16 first MR images have been measured. For example, second MR images can already be generated during the measurement of the 16 first MR images, in particular in real time. The second MR images can furthermore be generated even if it had not been possible to measure all 16 first MR images, for example due to image artifacts or other interferences.

For example, an MR signal can then be determined at different points in time by means of the second MR images and the signal course over time can thus be determined voxel by voxel/pixel by pixel. Different parameters, which are relevant for the clinical diagnosis, can then be determined from these signal-time curves voxel by voxel/pixel by pixel. Examples for this are described, for example in Buxton, R. B. et al., 1998. A general kinetic model for quantitative perfusion imaging with arterial spin labeling. *Magnetic Resonance in Medicine*, 40(3), pages 383-96.

The MR system 1 shown in FIG. 1 furthermore has a control unit 8, which is adapted to control the different units of the MR system 1, and an input unit 9, such as a keyboard, a computer mouse, a touch screen, etc., for example. In addition, the MR system 1 comprises an output unit 25, such as a monitor, for example.

Figure 3:
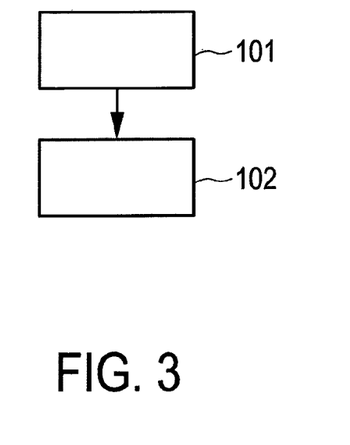
FIG. 3 shows an embodiment of an evaluation system for evaluating first MR data in a schematic and exemplary manner and FIG. 4 shows a flowchart, which illustrated an MR method in an exemplary manner.

An MR method for generating MR data of a flowing fluid will be described below with reference to a flowchart, which is illustrated in FIG. 3.

First MR data are collected in step 101, wherein a plurality of MR measurements is carried out and wherein first MR data are measured in each MR measurement. In particular, a first MR image is generated in each MR measurement, so as to measure first MR data. In response to the generation of the first MR data, the fluid is either magnetically labeled or not labeled at different first points in time in a first region, so as to generate a flowing sequence of labeled and/or unlabeled fluid boli. In addition, the first MR data, which are indicative of the generated sequence of labeled and/or unlabeled fluid boli, are measured at a second point in time in a second region, to which the fluid flows, starting at the first region. This means that a respective sequence of labeled and/or unlabeled fluid boli is created in each MR measurement and a first MR image is preferably generated as measurement of the first MR data for each of these sequences.

Second MR data, each of which are indicative of a combination fluid bolus—combined from a plurality of labeled/unlabeled fluid boli generated at different first points in time and flowing to the second region—and a time interval TI between one of the first points in time and the second point in time, are furthermore determined in step 101, in that the first MR data measured in the different MR measurements, are joined, as already described. Due to the fact that not all of the first MR data are required for determining these second MR data, second MR data for the combination fluid boli can already be determined during the acquisition of the first MR data, that is, of the first MR images, in this exemplary embodiment.

After the measurement of the first MR data has concluded, they can also be used in step 102 to determine those second MR data, each of which are indicative of an individual fluid bolus generated at a certain first point in time and flowing to the second region.

Figure 4:
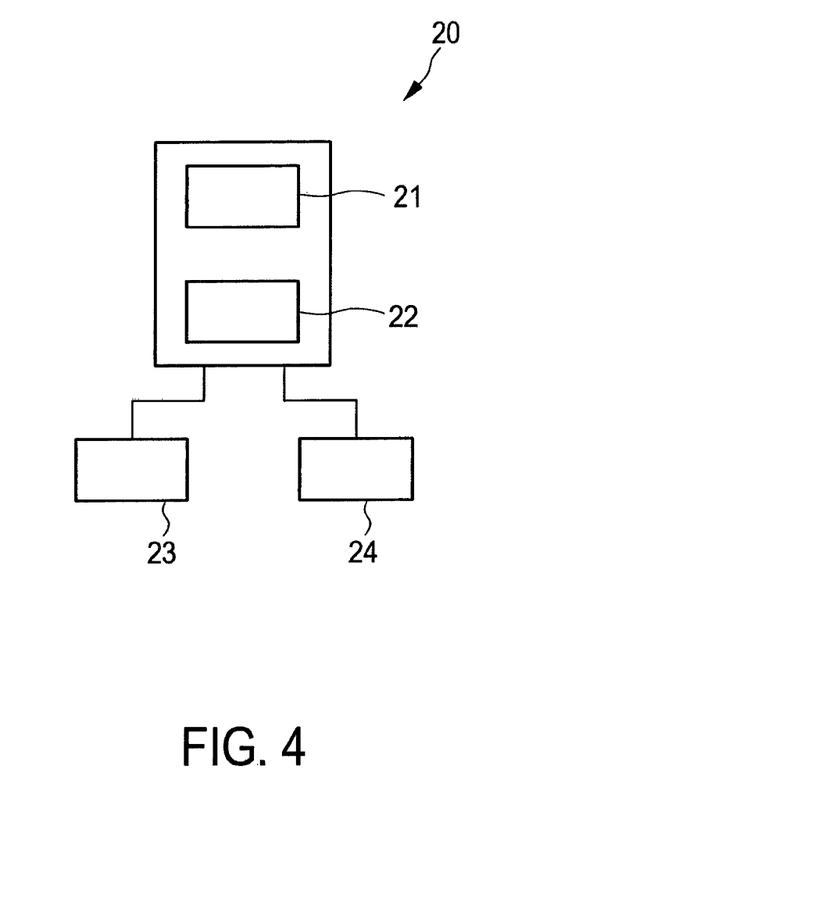

FIG. 4 shows an evaluation system 20 for evaluating MR data of a flowing fluid in a schematic and exemplary manner. The evaluation system 20 comprises a data provision unit 21 for providing first MR data, wherein the data provision unit 21 is adapted to provide first MR data from a plurality of MR measurements, and wherein first MR data were measured in each MR measurement, in that a) the fluid was either magnetically labeled or not labeled at different first points in time in a first region, so as to generate a flowing sequence of labeled and/or unlabeled fluid boli, and b) the first MR data, which are indicative of the generated sequence of labeled and/or unlabeled fluid boli, were measured at a second point in time in a second region, to which the fluid flows, starting at the first region. The evaluation system 20 furthermore comprises an evaluation unit 22, which corresponds to the above-described evaluation unit 7 of the MR system 1, for evaluating the first MR data measured in the different MR measurements. The evaluation unit 22 is adapted to determine second MR data, each of which are indicative of a combination fluid bolus—combined from a plurality of labeled/unlabeled fluid boli generated at different first points in time and flowing to the second region—and a time interval between one of the first points in time and the second point in time, based on the joining of the first MR data measured in the different MR measurements, as already described. The evaluation unit 22 is preferably also adapted to determine second MR data, each of which are indicative of an individual fluid bolus generated at a certain first point in time and flowing to the second region, based on a joining of the first MR data measured in the different MR measurements. The evaluation system 20 also comprises an input unit 23, such as a keyboard, a computer mouse or a touch screen, for example, and an output unit 24, such as a monitor, for example.

Even though the first MR data were only measured at a second point in time in the above-described embodiments, the first MR data can also be measured at a plurality of different second points in time in other embodiments.

For example, first MR data in each MR measurement can also be measured at a plurality of second points in time $t_1<t_2<t_3<\ldots$ . Second MR data can then be generated for each point in time $t_i$. The signal intensity, for example, could thus be determined at more points in time, namely the product of the number of second points in time and the number of second MR data, than would be possible with a measurement at only a second point in time. More data points would thus be available for a signal-time curve, which can improve a fitting, for example.

Some exemplary explanations relating to the individual aspects of the invention follow.

For example, the data recording unit can be adapted to effect a rotation of the blood magnetization about a desired angle, for labeling the blood at a first point in time and in a selected section, e.g. the carotid artery. In an exemplary embodiment, the magnetization resulting from the spins of the protons in the blood is rotated (inverted) from the relaxed state (0°) by 180°. This is also called labeling here. A clearly defined longitudinal section of the flowing blood (bolus, labeling region) is generated in this manner. The blood with inverted magnetization locally changes the magnetic properties at the locations, to which it flows, and thus the contrast of an MR image (label image) generated after the labeling. Due to the fact that these changes are very small and are not visible with the naked eye, an image is additionally generated without prior labeling, the so-called control image. The effects of perfusion and/or flow, for example, then become visible and, if applicable, also quantifiable in the difference of label and control image. In a further exemplary embodiment, a saturation (rotation by 90°) of the magnetization is effected instead of an inversion.

The rotation (also called incline or flip) of the magnetization can take place by means of a radio frequency pulse (RF pulse), for example. An example for such RF pulses is described in Payne, G. S. & Leach, M. O., 1997. Implementation and evaluation of frequency offset corrected inversion (FOCI) pulses on a clinical MR system. *Magnetic resonance in medicine,* 38(5), pages 828-33 and Dai, W. et al., 2008. Continuous flow-driven inversion for arterial spin labeling using pulsed radio frequency and gradient fields. *Magnetic resonance in medicine,* 60(6), pages 1488-97.

This technology for labeling the blood can be used, for example, for not only generating a single labeled or unlabeled fluid bolus prior to the measurement of an MR image. In fact, sequences of labeled and unlabeled fluid boli can be created and a plurality of MR measurements of first MR data can be carried out successively, wherein a different sequence of labeled and unlabeled fluid boli is potentially generated in every measurement. The concrete design of these sequences can be provided in the form of a matrix, for example, wherein the matrix entries provide the type of labeling (for example labeled or not labeled) and every row of the matrix corresponds to an MR measurement of first MR data.

For the exemplary description of the generation of first MR data, reference is also made to Gadian, D. G., 1996. *NMR & Its Applications to Living Systems* 2 Sub., Oxf.U.P.; Bernstein, M., King, K. & Zhou, X., 2004. *Handbook of MRI pulse sequences,* Academic Press. For further details of the labeling process and the generation of the first MR data, reference is made in an exemplary manner to Williams, D. S. et al., 1992. Magnetic resonance imaging of perfusion using spin inversion of arterial water. *Proceedings of the National Academy of Sciences of the United States of America,* 89(1), pages 212-6, Detre, J., Leigh, J. & Williams, D., 1996. Perfusion imaging. *Magnetic Resonance in Medicine,* 35(1), pages 70-9, Günther, M., 2007. *Habilitationsschrift.* Ruprechts-Karl-Universitat Heidelberg (Günther 2007) and Günther, M., Oshio, K. & Feinberg, D. A., 2005. Single-shot 3D imaging techniques improve arterial spin labeling perfusion measurements. *Magnetic resonance in medicine,* 54(2), pages 491-498.

To gain second MR data, for example, which are indicative of a combination blood bolus (hereinafter also referred to as second MR combination data), only partial quantities of all first MR data can be used from first MR data, and they can nonetheless be relevant for the clinical diagnostics. In other words, fewer first MR data are required in this example for the reconstruction of second MR combination data, than for the reconstruction of second MR data, which are based on individual fluid boli (hereinafter referred to as second MR individual data). For example, the following observation forms the basis for this. When writing down the calculation of the second MR combination data from second MR individual data arithmetically in symbols, this observation is revealed. If the second MR individual data are written in symbols, in turn, as combination of addition and subtraction of the first MR data in the case of this calculation, it follows that some of the first MR data are calculated to zero in pairs. It follows from this statement that the second MR combination data can be described as combination of addition and subtraction of partial quantities of first MR data, and that fewer first MR data are required for the determination of second MR combination data, than for the determination of second MR individual data. In terms of this example, the second MR combination data are generated directly from the first MR data (and not via the detour of generating second MR individual data). This can be advantageous as compared to the prior art, because the calculation of second MR combination data carried out in the evaluation unit, for example, can be accelerated. This is so, because, the detour via the calculation of the second MR individual data is not longer necessary as in ((Günther 2007). The second MR individual data thus only need to be generated, when the highest possible detail resolution, here in particular time resolution, is required. The robustness of the measurement can furthermore also be increased in this manner, for example. If, for example, several first MR data are inaccurate, for example because a patient has moved, or should not be available, second MR individual data cannot or can only be determined in an inaccurate manner, if applicable. Second MR combination data can nonetheless still be determined from the intact and available first MR data.

If, for example, the determination matrix can be inverted, that is, the matrix, which is inverse thereto, can be determined, it is possible to determine second MR individual and combination data with the help thereof and with the help of the vector consisting of first MR values. However, other exemplary ways are also possible for determining second MR individual and MR combination data from first MR data. One example is the above-explained exemplary arithmetic representation of the second MR combination data as symbolically written combination of addition and/or subtraction of first MR data.

The Hadamard matrix, which is described in alia in (Guenther 2012) or (Wolfram 2002), is an example for a possible determination matrix.

When selecting the determination matrixes for an original matrix, the matrix complementary thereto (complementary matrix), in the case of which labeled and unlabeled states are interchanged, can be used, for example. This has the following advantage as compared to the prior art, for example. Typically, only N−1 second MR data can be determined from N first MR data, second MR data, which are indicative of the first fluid bolus, for example, cannot be generated. When using the information from the original matrix and the complementary matrix, however, second MR individual data, which are indicative of all N fluid boli, can be generated. Second MR combination data, which are indicative of the combination fluid boli, which would include the first fluid bolus, can then also be generated from the first MR data. For example, this can also allow generating second MR combination data, which are indicative of the combination fluid bolus, which consists of all N individual fluid boli, from two MR measurements, namely of the first row of the original matrix and of the first row of the complementary matrix. A further possible embodiment of the determination matrix could be such that only certain lines of an original matrix alternate with the lines of the complementary matrix. The remaining lines of the original matrix would then not alternate in the determination matrix and in the order, in which they are in the original matrix. At a different location of the determination matrix, the remaining lines of the complementary matrix would additionally not alternate and would not be in the order, in which they are in the complementary matrix.

The so-called sequence sorting is an example for the sorting by the number of changes between labeled and unlabeled fluid boil. The rows are thereby sorted according to their sequence and the sequence is defined as the number of the sign changes (i.e. zero crossings) of the entries of the row. In the case of sequence sorted Hadamard matrixes, this can also be referred to as Walsh sorting in this context (see for example (Wolfram 2002) on this topic). By means of a sequence-sorted determination matrix, for example, the sequence of the MR measurements can be resorted in such a way that the first MR data required for generating second MR combination data are measured as early as possible. One advantage as compared to the prior art is, for example, that, on principle, second MR combination data can already be determined before all first MR data have been measured, which are required for determining the second MR individual data, and that they are already relevant for the clinical diagnostics. It is possible, for example, that the second MR combination data are already determined in real time during the measurement, because, if the first MR data are generated in a suitable sequence, second MR combination data can already be generated therefrom during the measurement. This allows the medical personnel accompanying the measurement, for example, to obtain first information at a very early point in time of the examination. If applicable, the ongoing measurement can then be changed and/or further diagnostic steps can be planned. The robustness of the measurement can thus also be increased here, for example. Movements of a patient, which can render the images unusable, typically increase with the measuring time. If the partial quantities of first MR data, which already allow a generation of second MR combination data, are thus generated at the earliest point in time, the likelihood decreases that all of the second MR individual and/or MR combination data cannot be generated or can only be generated in an inaccurate manner as a result of the movement of a patient.

In other words, it can thus be stated that it can be made possible, for example, to select the sequence of the MR measurements and/or of the evaluation steps such that the second MR data, which can be generated from the smallest possible number of first MR data, are determined initially. This number can even be minimal.

A general example for a Walsh sorting will be provided below.

The Walsh sorting can be carried out in three steps. For this purpose, a provided sequence S is initially written as binary number (also called dual number):

$$S = (S_{n-1}S_{n-2} \ldots S_1S_0)_2 = \sum_{i=0}^{n-1} S_i 2^i$$

This number in the binary code is then converted into Gray code:

$$g_i = S_i \oplus S_{i+1}, i \in [0, n-1], S_n = 0$$

⊕ thereby represents the exclusive or.
By means of a bit reversal $$k_i = g_{n-1-i}$$

the binary values $k_i$ are then determined from the $g_i$'s. The row number k of the Hadamard matrix, which belongs to the sequence, can then be determined from the binary representation $$k = (k_{n-1}k_{n-2} \ldots k_1k_0)_2 = \sum_{i=0}^{n-1} k_i 2^i.$$

If the lines k of the Hadamard matrix are arranged in such a manner that the sequences S, which belong to the k, increase or decrease, the matrix is called Walsh-sorted.

In particular for N=8 lines, the steps result in:

| S | 0 | 1 | 2 | 3 | 4 | 5 | 6 | 7 |
|---|---|---|---|---|---|---|---|---|
| binary | 000 | 001 | 010 | 011 | 100 | 101 | 110 | 111 |
| Gray code | 000 | 001 | 011 | 010 | 110 | 111 | 101 | 100 |
| Bit reverse | 000 | 100 | 110 | 010 | 011 | 111 | 101 | 001 |
| k | 0 | 4 | 6 | 2 | 3 | 7 | 5 | 1 |

If, for example, quantitative perfusion data are to be determined as well (see, for example (Buxton et al. 1998)), the evaluation unit can also provide for further arithmetic calculation operations for the further image processing.

For the sake of completeness, reference is also made to the following literature.

A method, which is very similar to Guenther 2012, is described in U.S. Pat. No. 8,610,433 B2.

It is proposed in Guenther 2007, to combine individual boli (labeling regions), referred to as subboli therein, into longer, so-called virtual (sub)boli. This is so, because an arbitrary, longer virtual (sub)bolus can be generated from the sum of a plurality of (sub)boli, and the distance for the image readout, the TI, also referred to as post labeling delay (PLD), can thus be varied additionally. In practice, all of the reconstructed MR images, which belong to the individual (sub)boli, are initially reconstructed from the measured MR images and are then added in a further reconstruction step to form twice-reconstructed MR images, so that the (sub)boli, which belong to the reconstructed MR images, form virtual (sub)boli, which belong to the twice-reconstructed MR images.

This and further aspects are described expressly in (Gunther 2007), Dai, W., Shankaranarayanan, A. & Alsop, D. C., 2013. Volumetric measurement of perfusion and arterial transit delay using hadamard encoded continuous arterial spin labeling. Magnetic resonance in medicine, 69(4), pages 1014-22 and Teeuwisse, W. M. et al., 2014. Time-encoded pseudocontinuous arterial spin labeling: Basic properties and timing strategies for human applications. *Magnetic resonance in medicine.*

In the claims, the words "have" and "comprise" do not exclude other elements or steps and the indefinite article "a" does not exclude a plurality.

An individual unit or device can carry out the functions of a plurality of elements, which are specified in the claims. The fact that individual functions and elements are specified in different dependent claims does not mean that a combination of these functions or elements could not also be used in an advantageous manner.

The control of the MR system and/or of the evaluation system according to the MR method or the evaluation method, respectively, can be implemented as program code of a computer program and/or as corresponding hardware.

A computer program can be stored and/or distributed on a suitable medium, such as, for example, an optical storage medium or a solid state storage medium, which is sold together with or as part of other hardware. However, the computer program can also be sold in other forms, for example via the Internet or other telecommunication systems.

The reference numerals in the claims are to not be understood in such a way that the subject matter and the scope of protection of the claims are limited by these reference numerals.

The invention claimed is:

1. A magnetic resonance system for generating magnetic resonance data of a flowing fluid, the magnetic resonance system comprising:
   a data collection unit, adapted to carry out a plurality of magnetic resonance measurements and thereby measures first magnetic resonance data $(v_i)$ in each magnetic resonance measurement, in that
a) the flowing fluid is either magnetically labeled or not labeled at different first points in time in a first region in such a manner that a flowing sequence of labeled (L) and/or unlabeled (C) fluid boli is generated, and
b) the first magnetic resonance data $(v_i)$, which are indicative of the generated sequence of labeled and/or unlabeled fluid boli (L, C), are measured at a second point in time in a second region, to which the flowing fluid flows, starting at the first region; and
   an evaluation unit, adapted to determine second magnetic resonance data $(K_i)$, each of which are indicative of a combination fluid bolus and a time interval (TI) between one of the first points in time and the second point in time, based on a joining of the first magnetic resonance data $(v_i)$ measured in the plurality of magnetic resonance measurements, wherein the combination fluid bolus is combined from a plurality of fluid boli (L, C) labeled/unlabeled at different first points in time and flowing to the second region.

2. The magnetic resonance system according to claim 1, wherein the evaluation unit (7) is furthermore adapted to determine second magnetic resonance data $(b_i)$, each of which are indicative of an individual fluid bolus (L, C) generated at a certain first point in time and flowing to the second region, based on a joining of the first magnetic resonance data $(v_i)$ measured in the plurality of magnetic resonance measurements.

3. The magnetic resonance system according to claim 1, wherein the evaluation unit is adapted in such a manner that fewer first magnetic resonance data $(v_i)$ are used to determine those second magnetic resonance data $(K_i)$, each of which are indicative of a combination fluid bolus and of a time interval (TI) between one of the first points in time and one of the second points in time, than are used to determine those second MR data $(b_i)$, each of which are indicative of an individual fluid bolus generated at a certain first point in time and flowing to the second region.

4. A magnetic resonance system according to claim 1, further comprising a matrix provision unit for providing a two-valued determination matrix, wherein one row of the determination matrix represents a sequence of labeled or unlabeled fluid boli (L, C), and different rows of the determination matrix form the basis for different magnetic resonance measurements of the first magnetic resonance data $(v_i)$, wherein the evaluation unit is furthermore adapted
   to form a vector, the vector elements of which are each formed by a magnetic resonance value of the first magnetic resonance data $(v_i)$, and different vector elements correspond to different magnetic resonance measurements of the first magnetic resonance data $(v_i)$,
   to invert the determination matrix, and
   to determine the second magnetic resonance data, in that the inverted determination matrix is applied to the vector.

5. The magnetic resonance system according to claim 1, wherein the data collection unit is furthermore adapted to generate a sequence of labeled/unlabeled fluid boli (C, L), which is complementary to each sequence of labeled/unlabeled fluid boli (L, C).

6. The magnetic resonance system according to claim 5, wherein the data collection unit is furthermore adapted to carry out the magnetic resonance measurements of the first magnetic resonance data $(v_i)$ of complementary sequences one immediately after the other.

7. The magnetic resonance system according to claim 5, further comprising a matrix provision unit for providing two determination matrixes, each of which is two-valued, namely a first one, the rows of which represent a first group of sequences of labeled/unlabeled fluid boli (L, C), and wherein different rows of the first determination matrix form the basis for different magnetic resonance measurements of the first magnetic resonance data $(v_i)$, and a second determination matrix, the rows of which represent a second group of sequences of labeled/unlabeled fluid boli (C, L), which are complementary to the fluid boli sequences of the first group, and wherein different rows of the second determination matrix form the basis for different magnetic resonance measurements of the first magnetic resonance data $(v_i)$, wherein the evaluation unit is furthermore adapted
   to form a first vector, the vector elements of which are in each case formed by a magnetic resonance value of the first magnetic resonance data ($v_i$), and different vector elements of the first vector correspond to different magnetic resonance measurements of the first magnetic resonance data ($v_i$), which, in turn, correspond to different fluid boli sequences of the first group, to form a second vector, wherein a vector element of the second vector is formed by a magnetic resonance value of the first magnetic resonance data ($v_i$), and different vector elements of the second vector correspond to different magnetic resonance measurements of the first magnetic resonance data ($v_i$), which, in turn, correspond to different fluid boli sequences of the second group, to invert the first determination matrix and the second determination matrix, and to determine the second magnetic resonance data in that the inverted first determination matrix is applied to the first vector and the inverted second determination matrix is applied to the second vector.

8. The magnetic resonance system according to claim 1, wherein the data collection unit is furthermore adapted to carry out magnetic resonance measurements of the first magnetic resonance data ($v_i$) sorted chronologically one after the other according to the number of changes between labeled and unlabeled fluid boli (L, C) in the corresponding fluid boli sequences.

9. The magnetic resonance system according to claim 1, wherein the evaluation unit (7) is adapted to add the first magnetic resonance data ($v_i$) measured in the plurality of magnetic resonance measurements or to subtract them from one another, and to determine the second magnetic resonance data based on the addition and/or subtraction data obtained in this manner.

10. An evaluation system for evaluating magnetic resonance data of a flowing fluid, wherein the evaluation system comprises:

a data provision unit, adapted to provide first magnetic resonance data ($v_i$) of a plurality of magnetic resonance measurements, wherein first magnetic resonance data ($v_i$) are measured in each magnetic resonance measurement, in that a) the flowing fluid is either magnetically labeled or not labeled at different first points in time in a first region in such a manner that a flowing sequence of labeled (L) and/or unlabeled (C) fluid boli is generated, and b) the first magnetic resonance data ($v_i$), which are indicative of the generated sequence of labeled and/or unlabeled fluid boli (L, C), are measured at a second point in time in a second region, to which the flowing fluid flows, starting at the first region; and an evaluation unit, adapted to determine second magnetic resonance data ($K_i$), each of which are indicative of a combination fluid bolus and a time interval (TI) between one of the first points in time and the second point in time, based on a joining of the first magnetic resonance data ($v_i$) measured in the plurality of magnetic resonance measurements, wherein the combination fluid bolus is combined from a plurality of fluid boli (L, C) labeled/unlabeled at different first points in time and flowing to the second region.

11. The evaluation system according to claim 10, wherein the evaluation unit (7) is furthermore adapted to determine second magnetic resonance data ($b_i$), each of which are indicative of an individual fluid bolus (L, C) generated at a certain first point in time and flowing to the second region, based on a joining of the first magnetic resonance data (v) measured in the plurality of magnetic resonance measurements.

12. The evaluation system according to claim 10, wherein the evaluation unit is adapted in such a manner that fewer first magnetic resonance data ($v_i$) are used to determine those second magnetic resonance data ($K_i$), each of which are indicative of a combination fluid bolus and of a time interval (TI) between one of the first points in time and one of the second points in time, than are used to determine those second magnetic resonance data ($b_i$), each of which are indicative of an individual fluid bolus generated at a certain first point in time and flowing to the second region.

13. The evaluation system according to claim 10, further comprising a matrix provision unit for providing a two-valued determination matrix, wherein one row of the determination matrix represents a sequence of labeled or unlabeled fluid boli (L, C), and different rows of the determination matrix form the basis for different magnetic resonance measurements of the first magnetic resonance data ($v_i$), wherein the evaluation unit is furthermore adapted to form a vector, the vector elements of which are each formed by a magnetic resonance value of the first magnetic resonance data ($v_i$), and different vector elements correspond to different magnetic resonance measurements of the first magnetic resonance data ($v_i$), to invert the determination matrix, and to determine the second magnetic resonance data, in that the inverted determination matrix is applied to the vector.

14. The evaluation system according to claim 10, wherein the data provision unit is furthermore adapted to generate a sequence of labeled/unlabeled fluid boli (C, L), which is complementary to each sequence of labeled/unlabeled fluid boli (L, C).

15. The evaluation system according to claim 14, wherein the data provision unit is furthermore adapted to carry out the magnetic resonance measurements of the first magnetic resonance data ($v_i$) of complementary sequences one immediately after the other.

16. The evaluation system system according to claim 14, further comprising a matrix provision unit for providing two determination matrixes, each of which is two-valued, namely a first one, the rows of which represent a first group of sequences of labeled/unlabeled fluid boli (L, C), and wherein different rows of the first determination matrix form the basis for different magnetic resonance measurements of the first magnetic resonance data ($v_i$), and a second determination matrix, the rows of which represent a second group of sequences of labeled/unlabeled fluid boli (C, L), which are complementary to the fluid boli sequences of the first group, and wherein different rows of the second determination matrix form the basis for different magnetic resonance measurements of the first magnetic resonance data ($v_i$), wherein the evaluation unit is furthermore adapted to form a first vector, the vector elements of which are in each case formed by a magnetic resonance value of the first magnetic resonance data ($v_i$), and different vector elements of the first vector correspond to different magnetic resonance measurements of the first magnetic resonance data ($v_i$), which, in turn, correspond to different fluid boli sequences of the first group, to form a second vector, wherein a vector element of the second vector is formed by a magnetic resonance value of the first magnetic resonance data ($v_i$), and different vector elements of the second vector correspond to different magnetic resonance measurements of the first magnetic resonance data ($v_i$), which, in turn, correspond to different fluid boli sequences of the second group,
to invert the first determination matrix and the second determination matrix, and
to determine the second magnetic resonance data in that the inverted first determination matrix is applied to the first vector and the inverted second determination matrix is applied to the second vector.

17. The evaluation system according to claim 10, wherein the data provision unit is furthermore adapted to carry out magnetic resonance measurements of the first magnetic resonance data ($v_i$) sorted chronologically one after the other according to the number of changes between labeled and unlabeled fluid boli (L, C) in the corresponding fluid boli sequences.

18. The evaluation system according to claim 10, wherein the evaluation unit (7) is adapted to add the first magnetic resonance data ($v_i$) measured in the plurality of magnetic resonance measurements or to subtract them from one another, and to determine the second magnetic resonance data based on the addition and/or subtraction data obtained in this manner.

19. A magnetic resonance method for generating magnetic resonance data of a flowing fluid, wherein the magnetic resonance method comprises the steps of:
collecting first magnetic resonance data ($v_i$), wherein a plurality of magnetic resonance measurements are carried out and first magnetic resonance data ($v_i$) are measured thereby in each magnetic resonance measurement, in that
a) the flowing fluid is either magnetically labeled or not labeled at different first points in time in a first region in such a manner that a flowing sequence of labeled (L) and/or unlabeled (C) fluid boli is generated, and
b) the first magnetic resonance data ($v_i$), which are indicative of the generated sequence of labeled and/or unlabeled fluid boli (L, C), are measured at a second point in time a second region, to which the flowing fluid flows, starting at the first region; and
evaluating the first magnetic resonance data ($v_i$) measured in the plurality of magnetic resonance measurements, wherein the evaluation unit is adapted to determine second magnetic resonance data ($K_i$), each of which are indicative of a combination fluid bolus and a time interval (TI) between one of the first points in time and the second point in time, based on a joining of the first magnetic resonance data ($v_i$) measured in the plurality of magnetic resonance measurements, wherein the combination fluid bolus is combined from a plurality of fluid boli (L, C) labeled/unlabeled at different first points in time and flowing to the second region.

20. An evaluation method for evaluating magnetic resonance data of a flowing fluid, wherein the evaluation method comprises the steps of:
providing first magnetic resonance data ($v_i$), wherein a plurality of magnetic resonance measurements were carried out and first magnetic resonance data ($v_i$) were measured thereby in each magnetic resonance measurement, in that
a) the flowing fluid was either magnetically labeled or not labeled at different first points in time in a first region, so as to generate a flowing sequence of labeled (L) and/or unlabeled (C) fluid boli, and
b) the first magnetic resonance data ($v_i$), which are indicative of the generated sequence of labeled and/or unlabeled fluid boli (L, C), were measured at a second point in time in a second region, to which the flowing fluid flows, starting at the first region; and
evaluating the first magnetic resonance data ($v_i$) measured in the different magnetic resonance measurements in such a manner that second magnetic resonance data ($K_i$) are determined, each of which are indicative of a combination fluid bolus and a time interval (TI) between one of the first points in time and the second point in time, based on a joining of the first magnetic resonance data ($v_i$) measured in the plurality of magnetic resonance measurements, wherein the combination fluid bolus is combined from a plurality of fluid boli (L, C) labeled/unlabeled at different first points in time and flowing to the second region.

21. A non-transitory computer readable memory medium containing a computer program for generating magnetic resonance data of a flowing fluid, wherein the computer program comprises a program code that is operable to cause a magnetic resonance system to carry out a magnetic resonance method for generating magnetic resonance data of a flowing fluid, when the computer program is executed on a computer processor of a computer system, which controls the magnetic resonance system,
wherein the magnetic resonance method comprises the steps of:
collecting first resonance data ($v_i$), wherein a plurality of magnetic resonance measurements are carried out and first magnetic resonance data ($v_i$) are measured thereby in each magnetic resonance measurement, in that
a) the flowing fluid is either magnetically labeled or not labeled at different first points in time in a first region in such a manner that a flowing sequence of labeled (L) and/or unlabeled (C) fluid boli is generated, and
b) the first magnetic resonance data ($v_i$), which are indicative of the generated sequence of labeled and/or unlabeled fluid bob (L,C), are measured at a second point in time in a second region, to which the flowing fluid flows, starting at the first region; and
evaluating the first magnetic resonance data ($v_i$) measured in the plurality of magnetic resonance measurements, wherein the evaluation unit is adapted to determine second magnetic resonance data ($K_i$), each of which are indicative of a combination fluid bolus and a time interval (TI) between one of the first points in time and the second point in time, based on a joining of the first magnetic resonance data ($v_i$) measured in the plurality of magnetic resonance measurements, wherein the combination fluid bolus is combined from a plurality of fluid boli (L, C) labeled/unlabeled at different first points in time and flowing to the second region.

22. A non-transitory computer readable memory medium containing a computer program for evaluating magnetic resonance data of the flowing fluid,
wherein the computer program comprises a program code that is operable to cause an evaluation system to carry out an evaluation method for evaluating magnetic resonance data of the flowing fluid when the computer program is executed on a computer processor of a computer system which controls the evaluation system;
wherein the evaluation method comprises the steps of
providing first magnetic resonance data ($v_i$), wherein a plurality of magnetic resonance measurements were carried out and first magnetic resonance data ($v_i$) were measured thereby in each magnetic resonance measurement, in that a) the flowing fluid was either magnetically labeled or not labeled at different first points in time in a first region, so as to generate a flowing sequence of labeled (L) and/or unlabeled (C) fluid boli, and b) the first magnetic resonance data ($v_i$), which are indicative of the generated sequence of labeled and/or unlabeled fluid boli (L, C), were measured at a second point in time in a second region, to which the flowing fluid flows, starting at the first region; and evaluating the first magnetic resonance data ($v_i$) measured in the plurality of magnetic resonance measurements in such a manner that second magnetic resonance data ($K_i$) are determined, each of which are indicative of a combination fluid bolus and a time interval (TI) between one of the first points in time and the second point in time, based on a joining of the first magnetic resonance data ($v_i$) measured in the plurality of magnetic resonance measurements, wherein the combination fluid bolus is combined from a plurality of fluid boli (L, C) labeled/unlabeled at different first points in time and flowing to the second region.

* * * * *

UNITED STATES PATENT AND TRADEMARK OFFICE
CERTIFICATE OF CORRECTION

PATENT NO. : 10,473,745 B2
APPLICATION NO. : 15/128532
DATED : November 12, 2019
INVENTOR(S) : Federico Von Samson-Himmelstjerna and Matthias Guenther Page 1 of 1

It is certified that error appears in the above-identified patent and that said Letters Patent is hereby corrected as shown below:

In the Claims

Column 21, Claim 11, Line 65:
Delete: "second magnetic resonance data (b),"
Insert: --second magnetic resonance data $(b_i)$,--

Column 22, Claim 11, Line 1:
Delete: "first magnetic resonance data (v)"
Insert: --first magnetic resonance data $(v_i)$--

Column 22, Claim 16, Line 41:
Delete: "evaluation system system"
Insert: --evaluation system--

Column 23, Claim 19, Line 39:
Delete: "second point in time a second"
Insert: --second point in time in a second--

Column 24, Claim 21, Line 28:
Delete: "collecting first resonance data $(v_i)$"
Insert: --collecting first magnetic resonance data $(v_i)$--

Signed and Sealed this
Thirty-first Day of March, 2020

Andrei Iancu
*Director of the United States Patent and Trademark Office*